(12) United States Patent
Zhang et al.

(10) Patent No.: US 9,896,684 B2
(45) Date of Patent: Feb. 20, 2018

(54) DEVICE FOR NUCLEIC ACID EXTRACTION USING MAGNETIC BEAD METHOD

(71) Applicant: SANWAY GENE TECH INC., Changsha (CN)

(72) Inventors: Hongjian Zhang, Changsha (CN); Llzhong Dai, Changsha (CN)

(*) Notice: Subject to any disclaimer, the term of this patent is extended or adjusted under 35 U.S.C. 154(b) by 0 days.

(21) Appl. No.: 15/622,673

(22) Filed: Jun. 14, 2017

(65) Prior Publication Data
US 2017/0275614 A1    Sep. 28, 2017

Related U.S. Application Data

(63) Continuation of application No. PCT/CN2015/087791, filed on Aug. 21, 2015.

(30) Foreign Application Priority Data

Jan. 14, 2015  (CN) .......................... 2015 1 0017498

(51) Int. Cl.
*C12N 15/10* (2006.01)
*B03C 1/06* (2006.01)

(52) U.S. Cl.
CPC ............ *C12N 15/1013* (2013.01); *B03C 1/06* (2013.01); *B03C 2201/18* (2013.01)

(58) Field of Classification Search
CPC ................... B01L 2400/0409; B01L 3/50273; B01L 3/502738; B01L 2300/0803; B01L 2400/043; G01N 35/00069; C12N 15/1013; B03C 1/06; B03C 2201/18
See application file for complete search history.

(56) References Cited

U.S. PATENT DOCUMENTS

2008/0073546 A1 *  3/2008  Andersson .......... B01F 13/0059
250/396 ML

* cited by examiner

*Primary Examiner* — Sally A Merkling
(74) *Attorney, Agent, or Firm* — Wayne & Ken, LLC; Tony Hom

(57) ABSTRACT

The present invention provides a device for nucleic acid extraction using a magnetic bead method. The device includes a disc turntable, an arc arch bridge base, a supporting column, and a magnet structural unit and a sample reaction unit both arranged on the disc turntable. The disc turntable includes a top plate; the arc arch bridge base includes a bottom plate arranged at the lowermost portion and an arc supporting plate arranged on the bottom plate, and the arc supporting plate corresponds to the guide rod insertion holes in position in a radial direction of the disc, and the arc supporting plate includes raised regions used for jacking up a guide rod and a magnet and groove regions used for allowing the guide rod and the magnet to fall. The device provided by the present invention can realize the automatic nucleic acid extraction in a stream-lining manner.

10 Claims, 5 Drawing Sheets

DEVICE FOR NUCLEIC ACID EXTRACTION USING MAGNETIC BEAD METHOD

TECHNICAL FIELD

The present invention relates to the field of devices for extracting nucleic acid, and in particular relates to a device for nucleic acid extraction using a magnetic bead method.

BACKGROUND OF THE INVENTION

In a diagnostic process of infectious and hereditary diseases, molecular detection (such as nucleic acid detection) can remarkably shorten a detection window period and improve detection sensitivity. Generally, the quality (such as purity, etc.) of an analyte obtained from a specimen is an important factor which affects a detection result. For the nucleic acid detection, an amount and purity of the nucleic acid extracted from the specimen directly affect a result of the subsequent PCR (polymerase chain reaction) detection.

The nucleic acid is generally extracted through the following steps: 1) pyrolysis of a membrane covering the nucleic acid and release of the nucleic acid; 2) removal of proteins; and 3) collection of the nucleic acid. Classical methods include a boiling pyrolysis method and a phenol-chloroform extraction method. In the boiling pyrolysis method, a precipitant is first added into a sample, and after the centrifuging, a supernatant is removed so as to remove small-molecular inhibitors and precipitate virus particles; and then pyrolysis liquid is added and boiled so as to release DNA and precipitate macromolecular inhibitors such as residual proteins, etc., and centrifuging is performed to obtain the supernatant, i.e., DNA, in the phenol-chloroform extraction method, the pyrolysis liquid is first added into the sample; after chloroform is added, centrifuging is carried out so as to release RNA and enable the RNA to be separated from an albumen layer; and then the supernatant is added into isopropanol so as to extract the RNA; after the centrifuging, the supernatant is removed, and after ethanol is added for washing, the RNA is obtained. Since the two methods are complex in steps and involve in repeated centrifuging or heating, the automation is inconvenient to realize, and the manual labor intensity is high. On this basis, a method for extracting the nucleic acid with a membrane technology exists, which simplifies the operation, and can realize the automation. However, when the membrane is used to wash and collect the nucleic acid, a centrifugal machine is still needed, which is a major limitation of the method.

With the development of the materials science, a nano-meter particle (magnetic bead) is used for the nucleic acid extraction process. The paramagnetic nano particle can specifically or non-specifically adsorb the nucleic acid, and can conveniently separate the nucleic acid from a water phase by using a magnetic field, thereby achieving a purpose of extracting the nucleic acid. Once this material is used, it may cause the research and development of the automatic nucleic acid extraction technology. Various automatic nucleic acid extraction technologies and devices based on the nanomagnetic particles emerge. For example, nucleic acid extraction steps specifically include: in a sample containing the nucleic acid, 1) pyrolysis: the pyrolysis liquid is added; after the nucleic acid is pyrolysed from the sample, 2) combination: magnetic beads are added, and the magnetic beads are specifically combined with the nucleic acid; 3) washing: washing liquid is added, impurities such as proteins, etc. on the nucleic acid are removed through the washing step; 4) elution: elution liquid is added to separate the magnetic beads and the nucleic acid; and 5) separation: the magnetic beads are separated and gathered in a magnetic field so as to obtain the purified nucleic acid. However, considerable operation steps correspond to the nucleic extraction steps. Specifically, the pyrolysis liquid, the magnetic beads and the sample are first placed in a beaker (or a sample tube); a magnetic stick (rod-shaped magnet) and a disposable tip sleeved at one end of the magnetic stick are cooperatively placed into the beaker containing the above solution; the magnetic stick and the tip thereof are enabled to slowly move up and down so as to collect combinations of the magnetic heads and the nucleic acid; then the magnetic stick and the tip are collectively transferred into another solution (washing liquid); the magnetic stick is first taken out, so that the magnetic field disappears; and the tip moves up and down rapidly in the washing liquid, so that the combinations of, the magnetic, beads and the nucleic acid enter the solution. Then the magnetic stick is used to collect the combinations of the magnetic, beads, and the nucleic acid after being sleeved with the tip, and the magnetic stick and the tip are separated in the elution liquid. The obtained solution containing the magnetic beads and the nucleic acid is returned into the beaker so as to collect the magnetic beads and to obtain a pure nucleic acid solution.

That is, the cooperative application of the rod-shaped magnet and the disposable tip may transfer the magnetic heads from one reagent to another reagent. In a specific example, the above-mentioned rod-shaped magnets are arranged in an array (2 columns*8 rows, 4 columns*8 rows or 12 columns*8 rows); the disposable tip is arranged in an array of 1*8 or 12*8; and a reaction tube employs a 96-hole deep-hole plate. With respect to a working way, it can be divided into two types: one type is to employ the magnetic stick array of 2*8 or 4*8 and the disposable tip array of and an extraction process of 16 or 32 samples is completed in one deep-hole plate. The other type is to employ the magnetic stick array of 12*8 and the disposable tip array of 12*8; one extraction step (a reagent) is completed in one deep-hole plate; and the whole extraction process is completed collectively by using a plurality of deep-hole plates, and the extraction of 96 samples can be completed at one time.

When the magnetic separation device realizes the full automation of the entire extraction process, the cooperation of a liquid workstation is needed to distribute the sample and the reagent; or the reagent is pre-loaded in the deep-hole plate, and the sample is manually loaded. In addition, the above-mentioned magnetic-pen separation method still his many deficiencies: 1) the processing course of each independent sample is inconvenient to, track. Since a bath processing manner is adopted, a certain number of samples are simultaneously processed at different stages, and the failure of each sample in a batch at each stage cannot be correspondingly responded and processed in the processing course; and 2) in the case that the number of the samples is uncertain, the application efficiency is low, and the optimum performance can be obtained only under the designed processing throughput according to the number of magnetic pens and the design of the corresponding reaction vessels. If the number of the samples is smaller than the designed throughput, consumables may be wasted; and if the number of the samples is greater than the designed throughput, the re-operation is needed.

Another device for nucleic acid extraction using the magnetic bead method is a magnetic separation device carried on a liquid processing workstation. Such magnetic separation device generally consists of a square plate and rod-shaped magnets perpendicular to the plane of the square plate or strip-shaped magnets parallel to the plane in an array of a certain distance. The magnetic separation device can absorb the magnetic particles in each hole of the deep-hole plate onto the side wall, and can inject or transfer the reagent to complete the processing of different reagents by virtue of a liquid transfer mechanical arm of the liquid workstation, thereby completing the nucleic acid extraction process of one sample in a same hole.

Therefore, since all the devices fir nucleic acid extractions using the magnetic bead method in the prior art are manual or semiautomatic devices, the independent processing or the batch processing of the nucleic acid extraction can only be realized. Therefore, a hill-automatic device for nucleic acid extraction using the magnetic bead method needs to be provided in the art, and the device can be used to continuously extract the nucleic acid.

SUMMARY OF THE INVENTION

An objective of the present invention is to solve the problem for automatically extracting a target matter with an in vitro diagnostic reagent and automatically distributing the reagent and separating nanomagnetic particles in a detection process, and to provide a device convenient for automatically distributing the reagent and separating the nanomagnetic particles. By using the device, the distribution and the reaction of the reagent can be performed for an independent sample, and the solid-liquid two-phase separation can be performed for the magnetic nano particles absorbing the target matter; and the device can be conveniently applied to the automatic processing of the sample in the in Vitro diagnosis process using the magnetic nano particles.

Therefore, the present invention provides a device for nucleic acid extraction using a magnetic bead method. The device includes a disc turntable in an inverted disc shape, an arc arch bridge base disposed right below the disc turntable, a supporting column connecting the disc turntable and the arc arch bridge base and disposed in the center of a disc along a vertical direction, and a magnet structural unit and a sample reaction unit which are arranged on the disc turntable.

The disc turntable includes a top plate; the top plate is successively provided with guide rod insertion holes and sample reaction unit insertion holes from a circumference to a circle center.

The arc arch bridge base includes a bottom plate arranged at the lowermost side and an arc supporting plate arranged on the bottom plate, and the arc supporting plate corresponds to the guide rod insertion holes in position in a radial direction of the disc, and the arc supporting plate includes raised regions used for jacking up a guide rod and a magnet and groove regions used for allowing the guide rod and the magnet to fall.

The supporting column is arranged above the bottom plate.

The magnet structural unit includes a vertical guide rod, a magnet and a magnet support used for driving the magnet to move up and down synchronously when the guide rod moves up and down; the magnet support and the magnet are arranged below the top plate, and the magnet is arranged between the guide rod and the supporting column in the radial direction of the disc.

The sample reaction unit includes a sample tube supporting plate capable of being arranged on the sample reaction unit insertion holes, and a sample tube which is downward arranged on the sample tube support plate and is adjacent to the magnet in the radial direction of the disc.

Specifically, a top plane of the arc supporting plate corresponds to the guide rod insertion hole in position in the radial direction of the disc.

Preferably, 24 guide rod insertion holes and 24 sample reaction unit insertion holes are respectively provided and uniformly arranged in the circumferential direction of the top plate.

Preferably, 2 raised regions and 2 groove regions are respectively provided and uniformly arranged at intervals in the circumferential direction of the bottom plate.

In a specific embodiment, the sample reaction unit includes a sample tube and a reserved sample tube which are arranged at two ends in the radial direction of the disc, and a backup tube arranged in the middle. The backup tube 52, for example, is used for holding waste liquid in the nucleic acid extraction process. It will be appreciated by those skilled in the art that when the sample reaction unit 5 is horizontally turned for 180° along the radial direction of the disc and then arranged on the sample reaction unit insertion hole 112, the original reserved sample tube 54 becomes a sample tube 51.

In a specific embodiment, the sample tube is a cone tube with a large a upper portion and a small lower portion.

Preferably, the magnet is a strip-shaped magnet which is arranged in a vertically upward direction or in an obliquely upward direction.

In a specific embodiment, the sample reaction unit further includes a shielding frame 55 which is arranged above the sample tube supporting plate and used for preventing the cross infection of the samples among various sample reaction units.

Preferably, the disc turntable further includes a surrounding edge extending downward along the top plate, and the surrounding edge 12 is an arc-plate type surrounding edge or a surrounding edge with a regularly-polygonal top surface formed by connecting a plurality of rectangular plates in a head-to-tail manner.

In a specific embodiment, the bottom plate is a circular bottom plate or a hollow annular bottom plate.

Preferably, a length of the magnet is ½ to 1 time of the length of the sample tube, such as ⅔ time.

Preferably, the top plate is successively provided with guide rod insertion holes, sample reaction unit insertion holes and a supporting column insertion hole 113 from a circumference to a circle center.

In the above drawings, 1: disc turntable; 11: top plate; 111: guide rod insertion hole; 112: sample reaction unit insertion hole; 113: supporting column insertion hole; 12: surrounding edge; 2: arc arch bridge base; 21: bottom plate; 22: arc supporting Plate; 221: raised region; 222; groove region; 3: supporting column; 4: magnet structural unit; 41: guide rod; 42: magnet support; 43: magnet; 5: sample reaction unit; 51: sample tube; 52: backup tube; 53: sample tube supporting plate; 54: reserved sample tube; and 55: shielding frame.

DETAILED DESCRIPTION OF THE INVENTION

The objective of the present invention is realized through the following technical solution. The following embodiments are used to explain the present invention rather than limiting the protection scope of the present invention.

Figure 1:
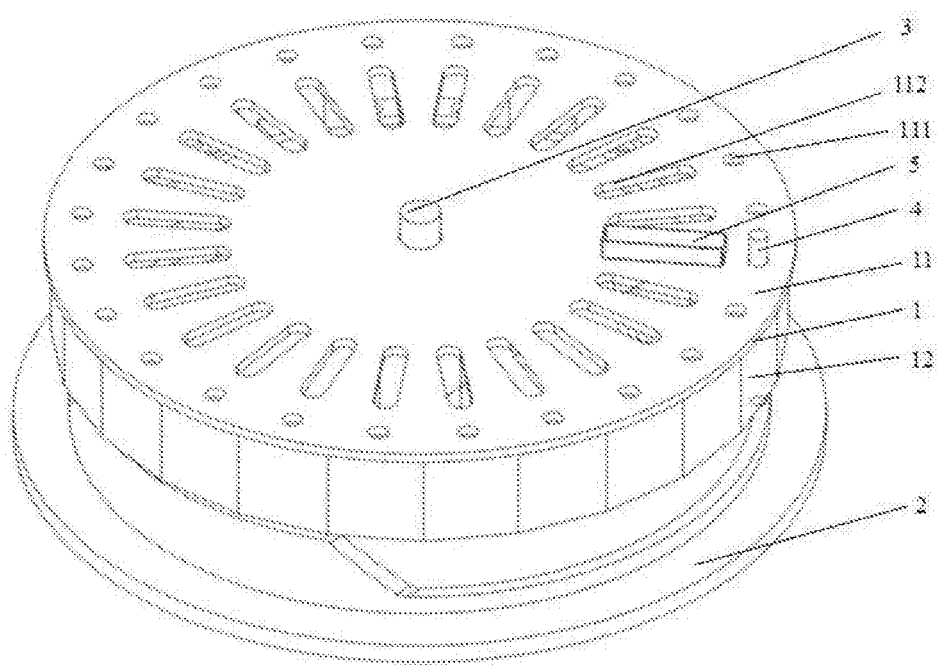
FIG. 1 is an overall structural schematic diagram illustrating a device for nucleic acid extraction using a magnetic bead method in present invention.
Figure 1A:
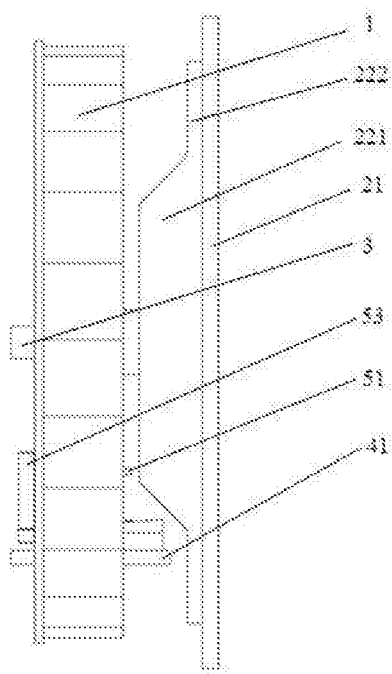
FIG. 1*a* and FIG. 1*b* are respectively a left side view and a right side view of FIG. 1.
Figure 1B:
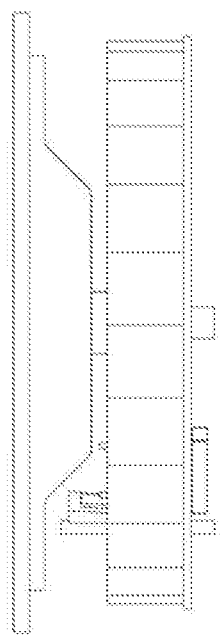
Figure 1C:
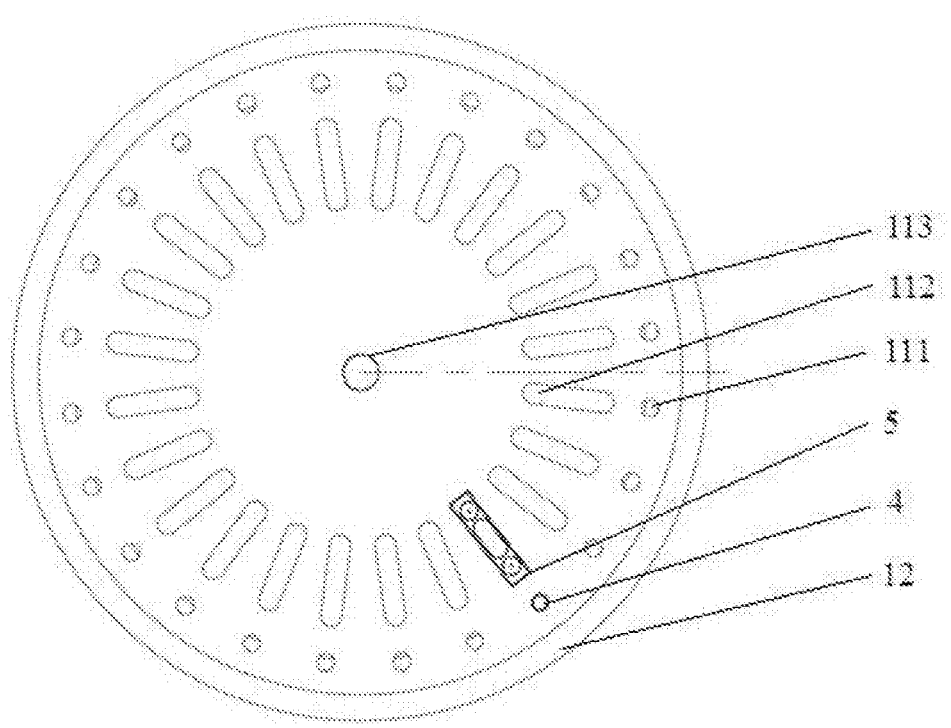
FIG. 1*c* is a top view of FIG. 1.

As shown in FIG. 1, the present invention provides a device for nucleic acid extraction using a magnetic bead method. The device includes a disc turntable in an inverted disc shape, an arc arch bridge base disposed right below the disc turntable, a supporting column connecting the disc turntable and the arc arch bridge base and disposed in the center of a disc along a vertical direction, and a magnet structural unit and a sample reaction unit which are arranged on the disc turntable, wherein the disc turntable includes a top plate, and the top plate is successively provided with guide rod insertion holes, sample reaction unit insertion holes and a supporting column insertion hole 113 in a direction from a circumference to a circle center; and the disc turntable further includes a surrounding edge extending downward along the top plate, and the surrounding edge 12 is an arc-plate type surrounding edge or a surrounding edge with a regularly-polygonal top surface formed by connecting a plurality of rectangular plates in ahead-to-tail manner.

Figure 1D:
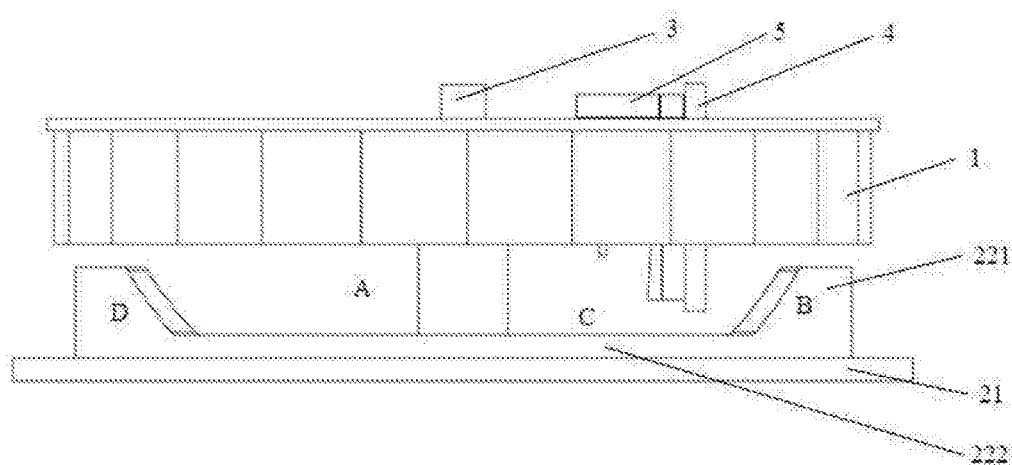
FIG. 1*d* is a front view of FIG. 1.
Figure 2:
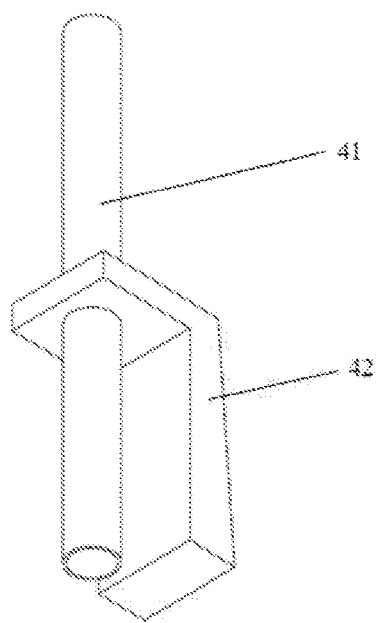
FIG. 2 is an overall structural schematic diagram illustrating a magnet structural unit in FIG. 1.
Figure 2A:
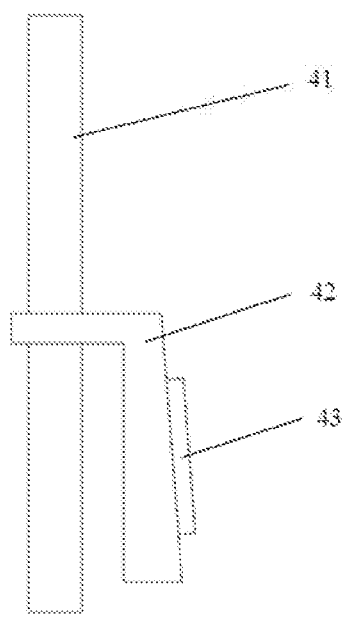
FIG. 2*a* is a front view of FIG. 2.
Figure 3:
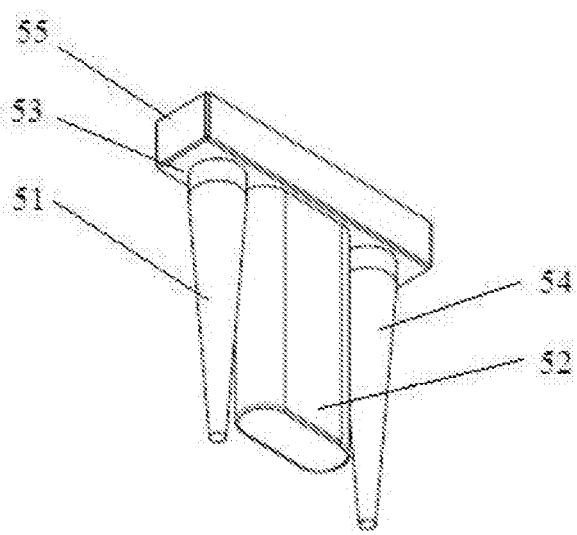
FIG. 3 is an overall structural schematic diagram illustrating a sample reaction unit in FIG. 1.
Figure 3A:
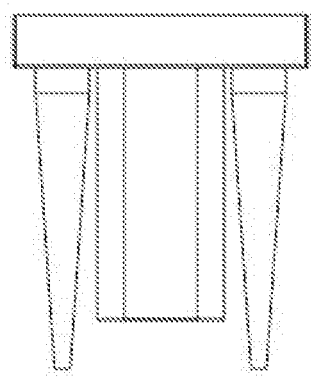
FIG. 3*a* is a front view of FIG. 3.
Figure 3B:
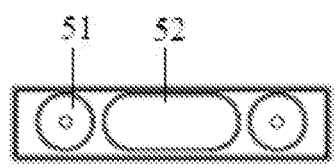
FIG. 3*b* is a top view of FIG. 3.

The arc arch bridge base includes a bottom plate arranged at the lowermost side and an arc supporting plate arranged on the bottom plate; the arc supporting plate corresponds to the guide rod insertion holes in position in a radial direction of the disc; the arc supporting plate includes raised regions used for jacking up a guide rod and a magnet and groove regions used for allowing the guide rod and the magnet to hit, and 2 raised regions and 2 groove regions are respectively provided and uniformly arranged at intervals in the circumferential direction of the bottom plate. In FIG. 1d, the raised region includes a region B and a region D, while the groove region includes a region A and a region C. The bottom plate is a circular bottom plate. The arc supporting plate refers to that the entire plate is in an arc shape; and specifically in the present embodiment, the shape of the arc supporting plate is part of a cylindrical barrel, an upper bottom surface and a lower bottom surface of the arc supporting plate are planes, and an outer side surface of the arc supporting plate is an arc wall of a cylinder.

The supporting column is arranged above the bottom plate. The magnet structural unit includes a vertical guide rod, a magnet and a magnet support used for driving the magnet to move up and down synchronously when the guide rod moves up and down: both the magnet support and the magnet are arranged below the top plate., and the magnet is arranged between the guide rod and the supporting column in the radial direction of the disc; and the magnet is a strip-shaped magnet which is arranged in a vertically upward direction or in an obliquely upward direction.

The sample reaction unit includes a sample tube supporting plate capable of being arranged on the sample reaction unit insertion holes, and a sample tube which is downward arranged on the sample tube support plate and is adjacent to the magnet in the radial direction of the disc. The sample reaction unit includes a sample tube and a reserved sample tube which are arranged at two ends in the radial direction of the disc, and a backup tube arranged in the middle. The backup tube 52, for example, is used for holding waste liquid in the nucleic acid extraction process. The sample tube is a cone tube with a large upper portion and a small lower portion. The sample reaction unit further includes a shielding frame 55 which is arranged above the sample tube support plate and used for preventing the cross infection of the samples among various sample reaction units.

24 guide rod insertion holes and 24 sample reaction unit insertion holes are respectively provided and uniformly arranged in the circumferential direction of the top plate. A length of the magnet is ⅔ time of the length of the sample tube.

An application method and a movement mode of the above device for nucleic acid extraction using the magnetic bead method are: when the disc turntable 1 rotates, and when a magnet structural unit 4 and a sample reaction unit 5 on the disc turntable 1 rotate to positions corresponding to the raised regions 221, the raised regions 221 jack up the guide rod 41, and the guide rod 41 drives the magnet 43 to move upwards to approach the sample tube 51, thereby applying a magnetic field, to the sample tube; arid when the magnet structural unit 4 and, the sample reaction unit 5 rotate to positions corresponding to the groove regions 222, the guide rod 41 falls downward, the guide rod 41 drives the magnet 43 to move downward, and the magnet is away from the sample tube 51 in the vertical direction, thereby removing the magnetic field from the sample tube.

In the present invention, the position of the magnetic field applied to the outer side wall of the sample tube 51 may also be changed by designing a height of the raised regions 221, thereby controlling a height position of gathering the nano-magnetic beads at the inner wall of the sample tube 51.

In FIG. 1d, the disc turntable 1 rotates to the region B, the region C and the region D from a position corresponding to the region A, and after the disc turntable 1 rotates for one cycle, a pyrolysis and washing process of the nucleic acid is realized. When the disc turntable rotates back, to the region A, PCR reaction liquid may be added to re-suspend a nucleic acid-magnetic bead composite and then transfer same into a PCR tube, and a PCR amplifier is used to perform the detection.

The device provided by the present invention can realize the automatic nucleic acid extraction in a stream-lining manner.

The above are only preferred embodiments of the present invention and are not used for limiting the present invention. For those skilled in the art, the present invention may have a variety of modifications and changes. Any modification, equivalent replacement, improvement and the like made within the spirit and the principle of the present invention shall be included in the protection scope of the present invention.

What is claimed is:

1. A device for nucleic acid extraction using a magnetic bead method, comprising a disc turntable (1) in an inverted disc shape, an arc arch bridge base (2) disposed right below the disc turntable (supporting column (3) connecting the disc turntable (1) and the arc arch bridge base (2) and disposed in a center of a disc along a vertical direction, and a magnet structural unit (4) and a sample reaction unit (5) both arranged on the disc turntable (1), wherein the disc turntable (1) comprises a top plate (11); the top plate (11) is successively provided with guide rod insertion holes (111) and sample reaction unit insertion holes (112) in a direction from a circumference to a circle center;

the arc arch bridge base (2) comprises a bottom plate (21) arranged at the lowermost side and an arc supporting plate (22) arranged on the bottom plate (21); the arc supporting plate (22) corresponds to the guide rod insertion holes (111) in position in a radial direction of the disc; the arc supporting plate (22) comprises raised regions (221) for lacking up a guide rod and a magnet and groove regions (222) for allowing the guide rod and the magnet to fall;

the supporting column (3) is arranged above the bottom plate (21);

the magnetic structural unit (4) comprises a vertical guide rod (41), a magnet (43) and a magnet support (42) for driving the magnet (43) to move up and down synchronously when the guide rod (41) moves up and down; both the magnet support (42) and the magnet (43) are arranged below the top plate (11), and the magnet (43) is arranged between the guide rod (41) and the supporting column (3) in the radial direction of the disc; and the sample reaction unit (5) comprises a sample tube supporting plate (53) capable of being arranged on the sample reaction unit insertion hole (112), and a sample tube (51) arranged downward from the sample tube supporting plate (53) and adjacent to the magnet (43) in the radial direction of the disc.

2. The device for nucleic acid extraction using the magnetic bead method according to claim 1, wherein 24 guide rod insertion holes (111) and 24 sample reaction unit insertion holes (112) are respectively provided and uniformly arranged in the circumferential direction of the top plate (11).

3. The device for nucleic acid extraction using the magnetic bead method according to claim wherein 2 raised regions (221) and 2 groove regions (222) are provided and uniformly arranged at intervals in the circumferential direction of the bottom plate (21).

4. The device for nucleic acid extraction using the magnetic bead method according to claim 1, wherein the sample tube (5) comprises a sample tube (51) and a reserved sample tube (54) arranged at two ends in the radial direction of the disc, and a backup tube (52) arranged in the middle.

5. The device for nucleic acid extraction using the magnetic bead method according to claim 1, wherein the sample tube (51) is a cone tube with a large upper portion and a small lower portion.

6. The device for nucleic acid extraction using the magnetic bead method according to claim 1, wherein the magnet (43) is a strip-shaped magnet arranged m a vertically upward direction or in an obliquely upward direction.

7. The device for nucleic acid extraction using the magnetic bead method according to claim 1, wherein the sample reaction unit (5) further comprises a shielding frame (55) arranged above the sample tube supporting plate (53) and used for preventing the cross infection of the samples among various sample reaction units (5).

8. The device for nucleic acid extraction using the magnetic bead method according to claim wherein the disc turntable (1) further comprises a surrounding edge (12) extending downward along the top plate (11), and the surrounding edge (12) is an arc-plate type surrounding edge or a surrounding, edge with a regularly-polygonal top, surface formed by connecting a plurality of rectangular plates in a head-to-tail manner.

9. The device for nucleic acid extraction using the magnetic bead method according to claim 1, wherein the bottom plate (21) is a circular bottom plate or a hollow annular bottom plate.

10. The device for nucleic acid extraction using the magnetic bead method according to claim 1, wherein a length of the magnet (43) is ½ to 1 time of the length of the sample tube (51).

* * * * *